United States Patent [19]

Derrenbacker

[11] 4,307,249
[45] Dec. 22, 1981

[54] PROCESS FOR THE SELECTIVE PREPARATION OF P-AMINOPHENOL FROM NITROBENZENE

[75] Inventor: Edward L. Derrenbacker, St. Louis, Mo.

[73] Assignee: Mallinckrodt, Inc., St. Louis, Mo.

[21] Appl. No.: 223,195

[22] Filed: Jan. 7, 1981

[51] Int. Cl.$^3$ .................. C07C 89/00; C07C 89/04
[52] U.S. Cl. ............................. 564/418; 564/297
[58] Field of Search ........................ 564/418, 297

[56] References Cited

U.S. PATENT DOCUMENTS

| | | | |
|---|---|---|---|
| 3,845,129 | 10/1974 | Reid | 564/418 X |
| 3,876,703 | 4/1975 | Harmetz et al. | 564/418 X |
| 4,051,187 | 9/1977 | Medcalf | 564/418 |

FOREIGN PATENT DOCUMENTS

| | | | |
|---|---|---|---|
| 854732 | 10/1970 | Canada | 564/418 |
| 856366 | 12/1960 | United Kingdom | 564/418 |
| 1009024 | 11/1965 | United Kingdom | 564/418 |

OTHER PUBLICATIONS

Messenger et al., "Chem. Ab.", Ab. No. 92:78553b.

*Primary Examiner*—John Doll
*Attorney, Agent, or Firm*—Grace J. Fishel; Roy J. Klostermann; Lynden N. Goodwin

[57] ABSTRACT

An improved process for preparing p-aminophenol by the catalytic hydrogenation of nitrobenzene in an aqueous acidic reaction medium containing a dimethylalkylamine oxide whereby the hydrogenation rate is increased and the selectivity of the reaction for p-aminophenol is improved.

10 Claims, No Drawings

PROCESS FOR THE SELECTIVE PREPARATION OF P-AMINOPHENOL FROM NITROBENZENE

The present invention relates to an improved process for the selective production p-aminophenol from nitrobenzene in an acidic reaction medium containing a dimethylalkylamine oxide as a surfactant.

An important commercial method for the preparation of p-aminophenol (PAP) involves the catalytic hydrogenation of nitrobenzene in a strongly acid medium. In the process the hydrogenation is preferably carried out in the presence of a 10-13% sulfuric acid solution containing a small amount of a surfactant such a dodecyltrimethylammonium chloride, and employing a platinum on carbon catalyst. The reaction is somewhat complex and yields, in addition to the desired PAP, a significant amount of aniline as well as a number of minor amine by-products.

In accordance with Benner U.S. Pat. No. 3,383,416, issued May 14, 1968, it is preferred that the hydrogenation reaction be interrupted prior to consumption of all of the nitrobenzene as the catalyst tends to suspend in the nitrobenzene layer. This is advantageous since the aqueous reaction mixture is immiscible with the nitrobenzene layer and the aqueous layer containing the PAP, aniline and the other minor amine by-products is readily separated from the catalyst-nitrobenzene layer by decantation. The PAP is then precipitated from the aqueous layer by neutralization.

As above mentioned, dodecyltrimethylammonium chloride is commercially used as a surfactant in the catalytic hydrogenation of nitrobenzene. Its use, however, leads to the formation of trace amounts of o- and p-chloroaniline due to the presence of chloride. Other impurities arise as a result of the fact that dodecyltrimethylammonium chloride is usually supplied as a water-/isopropyl alcohol solution which leads to the formation of small amounts of o- and p-isopropoxyaniline. Since some aniline is always produced as a by-product, it would be desirable if some other surfactant could be found which did not lead to the formation of o- and p-chloroaniline, o- and p-isopropoxyaniline or the like as these derivatives follow the aniline and contaminate it.

In view of the above, among the objects of the present invention may be noted the provision of an improved process for the production of p-aminophenol from nitrobenzene. Other objects and features will be in part apparent and in part pointed out hereinafter.

The invention accordingly comprises the methods hereinafter described, the scope of the invention being indicated by the subjoined claims.

The improved process of the present invention comprises a method for preparing p-aminophenol by the catalytic hydrogenation of nitrobenzene in an acidic aqueous reaction medium containing dimethylalkylamine oxide as a surfactant. For the purpose of the present invention, it is essential that the dimethylalkylamine oxide be water soluble and it is preferred that the alkyl groups contain from 8 to 20 carbon atoms. Suitable alkyl groups can be straight or branched chain, saturated or unsaturated, but it is preferred that 50% or more be n-dodecyl and it is particularly preferred that 95% or more be n-dodecyl groups.

The dimethylalkylamine oxide is preferably added as a water solution and should be present in an amount from 0.1 to 0.4% by volume based on the volume of the aqueous medium. Ordinarily from 0.2 to 0.3% by volume of dimethylalkylamine oxide is sufficient and no particular advantage is obtained by using more than about 0.25%.

The following example illustrates the invention.

EXAMPLE 1

Four different surfactants were tested in four separate runs, three of which are in accordance with the present invention and one of which is in accordance with the prior art. In Runs 1-3, the surfactant was a 30-35% by weight solution of a dimethylalkylamine oxide whose composition is as shown in Table 1. In Run 4, the surfactant was a 33% by weight solution of dodecyltrimethylammonium chloride in a water/isopropyl alcohol solution.

TABLE 1

| | Distribution of alkyl groups in dimethylalkylamine oxide used in Runs 1-3 | | |
|---|---|---|---|
| | Run 1 | Run 2 | Run 3 |
| n-octyl | 7 | — | — |
| n-decyl | 6 | 1 | 1 |
| n-dodecyl | 52 | 70 | 97 |
| n-tetradecyl | 19 | 24 | 2 |
| n-hexadecyl | 9 | 5 | — |
| n-octadecyl | 2 | — | — |

In each run, a mixture of 650 ml of distilled water, 0.250 g of 3% platinum on carbon catalyst and 2 ml of the above-described surfactant solution was charged into a 2 liter reaction vessel equipped for pressure hydrogenation, flushed with nitrogen and then heated to 70° C. under hydrogen. With vigorous agitation, 110 g of 95-98% reagent grade sulfuric acid was added over a 3-5 minute period, the temperature rising from 70° C. to 90°-95° C. 185 g of nitrobenzene was then added rapidly and the hydrogen pressure adjusted to about 10 inches of water. Hydrogenation of the reaction mixture was then carried out for seven hours at 85° C.

After 7 hours of hydrogenation, agitation was stopped and the flow of hydrogen turned off. The system was purged with nitrogen and allowed to cool. When the temperature had fallen below 60° C., the aqueous and nitrobenzene phases were separated, the catalyst remaining suspended in the nitrobenzene phase. A 5 ml portion of the aqueous phase was then removed and diluted to 50 ml with 10% by weight of sulfuric acid for PAP and aniline assays. The remainder of the aqueous phase was extracted with toluene (2×100 ml) to remove most of the residual dissolved nitrobenzene. The aqueous phase was then cooled, with stirring, to 4° C. and was then neutralized to pH 7-8 with ammonium hydroxide solution and stirred at 5°-10° C. for an hour to precipitate the PAP. The precipitated PAP was filtered off, washed once with distilled water (50 ml) and twice with reagent aniline (1×75 ml and 1×25 ml), and twice with toluene (2×100 ml), and then air dried. The results from the four runs are shown in Table 2.

TABLE 2

| | Product concentration in aqueous phase | | |
|---|---|---|---|
| | % nitrobenzene converted | PAP (mg/ml) | Ratio PAP/aniline |
| Run 1 | 62.0 | 92 | 4.3 |
| Run 2 | 68.6 | 98 | 4.1 |
| Run 3 | 75.2 | 102 | 4.5 |

TABLE 2-continued

| | Product concentration in aqueous phase | |
|---|---|---|
| % nitrobenzene converted | PAP (mg/ml) | Ratio PAP/aniline |
| Run 4  57.1 | 83 | 4.1 |

In view of the above, it will be seen that the several objects of the invention are achieved and other advantageous results obtained. As various changes could be made in the above methods without departing from the scope of the invention, it is intended that all matter contained in the description shall be interpreted as illustrative and not in a limiting sense.

What is claimed:

1. A method for preparing p-aminophenol, by the catalytic hydrogenation of nitrobenzene in an acidic aqueous reaction medium containing dimethylalkylamine oxide wherein said alkyl group contains from 8 to 20 carbon atoms.

2. The method of claim 1 wherein 50% or more of the alkyl groups are n-dodecyl.

3. The method of claim 2 wherein 95% or more of the alkyl groups are n-dodecyl.

4. The method of claim 1 wherein the catalyst comprises platinum on carbon.

5. The method of claim 4 wherein the reaction medium is acidified with sulfuric acid.

6. The method of claim 5 wherein from 0.1 to 0.4% by volume of dimethylalkylamine oxide, based on the aqueous medium, is used.

7. The method of claim 6 wherein from 0.2 to 0.3% by volume of dimethylalkylamine oxide, based on the aqueous medium, is used.

8. The method of claim 7 wherein about 0.25% by volume of dimethylalkylamine oxide, based on the aqueous medium, is used.

9. The method of claim 3 wherein the catalyst comprises platinum on carbon and wherein the reaction medium is acidified with sulfuric acid.

10. The method of claim 9 wherein about 0.25% by volume of dimethylalkylamine oxide, based on the aqueous medium, is used.

* * * * *